United States Patent
Reidenberg et al.

(10) Patent No.: US 7,125,884 B2
(45) Date of Patent: Oct. 24, 2006

(54) N-BUT-3-ENYL NORBUPRENORPHINE AND ITS USE AS ANALGESIC

(75) Inventors: Bruce E. Reidenberg, Rye, NY (US); Donna-Donigi Gale, Ridgefield, CT (US); Vinayak J. Srinivasan, Monsey, NY (US)

(73) Assignee: Euro-Celtique S.A., Luxembourg (LU)

( * ) Notice: Subject to any disclaimer, the term of this patent is extended or adjusted under 35 U.S.C. 154(b) by 245 days.

(21) Appl. No.: 10/469,553

(22) PCT Filed: Mar. 4, 2002

(86) PCT No.: PCT/US02/06766

§ 371 (c)(1),
(2), (4) Date: Aug. 29, 2003

(87) PCT Pub. No.: WO02/070524

PCT Pub. Date: Sep. 12, 2002

(65) Prior Publication Data

US 2004/0087605 A1 May 6, 2004

Related U.S. Application Data

(60) Provisional application No. 60/272,819, filed on Mar. 2, 2001.

(51) Int. Cl.
*A01N 43/42* (2006.01)
*A61K 31/44* (2006.01)
*C07D 489/12* (2006.01)

(52) U.S. Cl. .......................................... 514/279; 546/39
(58) Field of Classification Search .................. 546/39, 546/44, 38; 514/279
See application file for complete search history.

(56) References Cited

U.S. PATENT DOCUMENTS 3,285,914 A 11/1966 Gordon et al.

5,968,547 A 10/1999 Reder et al.

FOREIGN PATENT DOCUMENTS

WO WO 99/38869 A1 8/1999

OTHER PUBLICATIONS

J. Marton et al. "Herstellung von 6,14–Ethenomorphinan- –Derivaten" Monatshefte fur Chemie 125 (11), 1229–1239 (1994).

*Primary Examiner*—Johann Richter
*Assistant Examiner*—Chukwuma Nwaonicha
(74) *Attorney, Agent, or Firm*—Darby & Darby

(57) ABSTRACT

The present invention provides compound having the structure: and pharmaceutically acceptable salts or derivatives thereof, as well as compositions including such compounds. The invention also provides methods of (1) preventing pain, (2) treating pain, (3) inducing sedation, (4) treating opiate addiction, (5) treating opiate withdrawal (abstinence syndrome) and/or (6) treating cough in a patient in need thereof by administering a compound or composition of the invention.

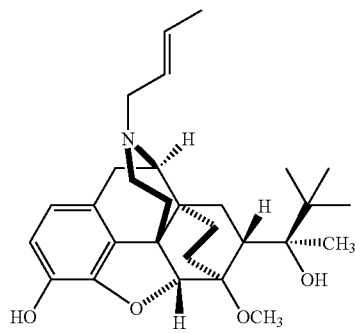

20 Claims, No Drawings

N-BUT-3-ENYL NORBUPRENORPHINE AND ITS USE AS ANALGESIC

CROSS-REFERENCE TO RELATED APPLICATION

This application claims priority from U.S. Provisional Application Ser. No. 60/272,819, filed Mar. 2, 2001, which is incorporated herein by reference in its entirety.

FIELD OF THE INVENTION

The present invention relates to a compound that has significant selectivity for μ opioid receptors versus δ, κ, and ORL-1 receptors; compositions and unit dosage forms of the compound; and methods of using such compound, compositions, and unit dosage forms.

BACKGROUND OF THE INVENTION

The opioid system modulates several physiological processes including analgesia, stress responses, immune responses, respiration, and neuroendocrine function (Herz, *Opioids* 1993, Vol. 1, Springer-Verlag, Berlin). Pharmacological and molecular cloning studies have identified four opioid receptor types (mu, delta, kappa, and ORL-1) that mediate these diverse effects (Miotto et al., The Pharmacology of Opioid Peptides (Ed. L. Tseng) 1995, 57–71, Harwood Acad. Publishers; Kieffer et al., Cell Mol. Neurobiol. 1995, 15:615–35). The opioid receptors are known to couple with pertussis toxin sensitive G-proteins to modulate adenylyl cyclase activity and potassium and calcium channel currents (Handbook of Experimental Pharmacology, Vol.104/I:Opioids I (Herz, A; Ed.) 1993, Springer-Verlag, Berlin; Duggan and North, Pharm. Rev. 1983, 35:219–282).

Most clinically used opiates are mu (μ) receptor ligands. For example, β-endorphins and enkephalins are endogenous ligands for the μ receptor. Dynorphin A also has high affinity for μ receptors, but has a higher affinity for kappa (κ) receptors (see below). Morphine and other morphine-like agonists produce analgesia primarily through interaction with μ receptors. Other physiological effects that are associated with μ receptor activation include, but are not limited to, respiratory depression, miosis, reduced gastrointestinal motility, and euphoria (Parternak, Clin. Neuropharmacol 1993, 16:1–18). In situ hybridization studies have shown that μ receptor mRNA is present in brain regions associated with pain perception (e.g., periaqueductal gray, spinal trigeminal nucleus, cunate and gracile nuclei, and thalamus), respiration (e.g., nucleus of the solitary tract, nucleus ambiguus, and parabrachial nucleus), and nausea and vomiting (e.g., neurons of the area postrema) (The Pharmacological Basis of Therapeutics, 9$^{th}$ edition (Eds Hardman, J G and Limbird, L E) 1996 McGraw-Hill, N.Y.). It is hypothesized that addiction to morphine and analgesics occurs through hyperactivation of μ receptors.

Subclasses of the κ receptor have been identified. In situ hybridization studies show that the $\kappa_1$ receptor subtype is predominantly present in hypothalamic regions, which accounts for receptor effects on neuroendocrine systems. Spinal activation of the $\kappa_1$ receptor subtype elicits analgesia in animal models. $\kappa_3$ receptor activation is also associated with analgesia, however it has been shown to produce its effects through supraspinal mechanisms (Clark, et al., J. Pharmacol. Exp. Ther. 1989, 251:461–468; Paul, et al., J. Pharmacol. Exp. Ther. 1991, 257:1–7). The $\kappa_2$ receptor subtype was identified based on binding studies, but the pharmacological effects of this receptor are currently unknown. Selective κ receptor ligands can induce analgesia that is undiminished by μ receptor tolerance. These ligands produce a majority of the observed pharmacological and physiological effects in the spinal cord and produce less intense respiratory depression than μ agonists. κ receptor agonists also produce neuroendocrine effects and dysphoric, psychomimetic effects (Pheiffer, A. et al., Science 1986, 233:744–746).

Two subclasses of the delta (δ) receptor have been identified, $\delta_1$ and $\delta_2$, based primarily on differential sensitivity to antagonists. Activation of these receptors produces analgesic effects through spinal and supraspinal mechanisms, although the spinal mechanism appears to be more robust. Activation of these receptors also produces positive reinforcing effects at supraspinal sites and antinociception for thermal stimuli at spinal sites (Pasternak, Clin. Neuropharmacol, 1993, 16:1–18). In situ hybridization studies have shown that the δ receptor is localized in the dorsal horn of the spinal cord.

A number of studies have demonstrated a broad spectrum of physiological functions of the ORL-1 receptor in both the central and peripheral nervous systems and in non-neuronal tissues. These functions include modulation of nociception (Meunier et al, Nature 1995, 377:532–5; Reinscheid et al., Science 1995, 270:792–794; Tian, et al., Br J Pharmacol 1998, 124:21–6), locomotor activity (Reinscheid et al., Science 1995, 270:792–794), reversal of stress-induced analgesia (Mogil, et al., Neuroscience 1996, 75:333–7), attenuation of stress responses (Jenck, et al., Proc Natl Acad Sci USA 1997, 94:14854–8), modulation of learning and memory (Mamiya, et al., Brain Res. 1998, 783:236–40; Manabe, et al., Nature 1998, 394:577–81; Sandin, et al., Eur J Neurosci 1997, 9:194–7), regulation of neurotransmitter and hormone release (Bryant, et al., Brain Res 1998, 807:228–33; Murphy, et al., Neuroscience 1996, 75:1–4), modulation of kidney function (Kapusta, et al., Life Sci 1997, 60:L15–21), and a potential role in neuronal differentiation (Buzas, et al., J Neurochem 1999, 72:1882–9; Saito, et al., Biochem Biophys Res Commun 1995, 217:539–45; Saito, et al., J Bio Chem 1996, 271:15615–22).

There is a continuing need in the art to develop ligands that are highly selective for one opioid receptor versus another. Development of such ligands will allow for further understanding of the pharmacology of these receptors. Additionally, such selective ligands may represent novel drugs for the treatment of pain, cough, and/or addiction that minimize adverse effects due to interaction with other opioid receptors.

SUMMARY OF THE INVENTION

The present invention contemplates a compound (I) having the structure:

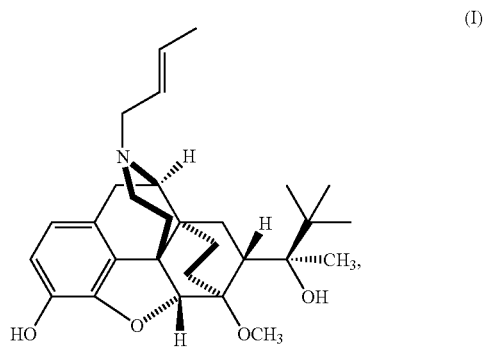

(I)

and a pharmaceutically acceptable salt, ether derivative, ester derivative, acid derivative, enantiomer, diastereomer, racemate, polymorph, or solvate thereof.

The present invention also contemplates a composition comprising a compound with the structure of formula (I) or salts or derivatives thereof.

The present invention contemplates a composition comprising a compound with the structure of formula (I) or a salt or derivative thereof, and further comprising: an adjuvant; an anti-oxidant; a buffer; a carrier; a colorant; a diluent; a disintegrant; an excipient; a filler; a flavorant; a gelling agent; a lubricant; a neutralizing agent; a preservative; or any combination of any of the foregoing.

The present invention contemplates a composition comprising (a) a compound with the structure of formula (I) or a salt or derivative thereof, and further comprising (b) an adjuvant; an anti-oxidant; a buffer; a carrier; a colorant; a diluent; a disintegrant; an excipient; a filler; a flavorant; a gelling agent; a lubricant; a neutralizing agent; a preservative; or any combination of any of the foregoing, wherein the compound is present in an opioid receptor agonizing effective amount.

The present invention contemplates a composition comprising (a) a compound with the structure of formula (I) or a salt or derivative thereof, and further comprising (b) an adjuvant; an anti-oxidant; a buffer; a carrier; a colorant; a diluent; a disintegrant; an excipient; a filler; a flavorant; a gelling agent; a lubricant; a neutralizing agent; a preservative; or any combination of any of the foregoing; wherein the compound is present in a $\mu$ opioid receptor agonizing effective amount.

The present invention contemplates a composition comprising (1) an analgesic effective amount, (2) a sedative effective amount, (3) an opiate addiction treatment effective amount, (4) an opiate withdrawal-relieving effective amount and/or (5) an anti-tussive effective amount of a compound with the structure of formula (I) or a salt or derivative thereof, and further comprising: an adjuvant; an anti-oxidant; a buffer; a carrier; a colorant; a diluent; a disintegrant; an excipient; a filler; a flavorant; a gelling agent; a lubricant; a neutralizing agent; a preservative; or any combination of any of the foregoing.

The present invention contemplates a composition comprising (1) an analgesic effective amount, (2) a sedative effective amount, (3) an opiate addiction treatment effective amount, (4) an opiate withdrawal-relieving effective amount and/or (5) an anti-tussive effective amount of a compound with the structure of formula (I) or a salt or derivative thereof, and further comprising: an adjuvant; an anti-oxidant; a buffer; a carrier; a colorant; a diluent; a disintegrant; an excipient; a filler; a flavorant; a gelling agent; a lubricant; a neutralizing agent; a preservative; or any combination of any of the foregoing; wherein the compound is from about 0.1 mg to about 1000 mg. Alternatively, the compound is provided in the composition in such as way as to achieve a maximum blood plasma concentration of about 20 pg/ml to about 10 ng/ml.

The present invention also contemplates a unit dosage form comprising a composition comprising a compound with the structure of formula (I) or a salt or derivative thereof.

The present invention also contemplates a unit dosage form comprising a composition comprising a compound with the structure of formula (I) or a salt or derivative thereof, wherein the unit dosage form is selected from the group consisting of tablets, pills, capsules, boluses, powders, granules, sterile parenteral solutions, sterile parenteral suspensions, elixirs, tinctures, metered aerosol, liquid sprays, drops, ampoules, autoinjector devices, suppositories, transdermal patches, and a lyophilized composition.

The present invention also contemplates a unit dosage form comprising a composition comprising a compound with the structure of formula (I) or a salt or derivative thereof, where the unit dosage form is a sustained release dosage unit form.

The present invention contemplates a method of stimulating $\mu$ opiate receptors in a patient in need thereof, the method comprising administering a $\mu$ opiate receptor agonizing effective amount of a composition comprising a compound with the structure of formula (I) or a salt or derivative thereof to the patient.

The present invention also contemplates a method of stimulating $\mu$ opiate receptors in a patient in need thereof, the method comprising administering a $\mu$ opiate receptor agonizing effective amount of a composition comprising a compound with the structure of formula (I) or a salt or derivative thereof to the patient, where the administration is selected from the group consisting of oral, intravenous, intramuscular, subcutaneous, transdermal, pulmonary, ophthalmic, transmucosal, and buccal administration.

The present invention also contemplates a method of (1) preventing pain, (2) treating pain, (3) inducing sedation, (4) treating opiate addiction, (5) treating opiate withdrawal (abstinence syndrome) and/or (6) treating cough in a patient in need thereof, the method comprising administering an effective amount of a composition comprising a compound with the structure of formula (I) or a salt or derivative thereof to the patient.

The present invention also contemplates a method of (1) preventing pain, (2) treating pain, (3) inducing sedation, (4) treating opiate addiction, (5) treating opiate withdrawal (abstinence syndrome) and/or (6) treating cough in a patient in need thereof, the method comprising administering an effective amount of a composition comprising a compound with the structure of formula (I) or a salt or derivative thereof to the patient, where the administration is selected from the group consisting of oral, intravenous, intramuscular, subcutaneous, transdermal, pulmonary, ophthalmic, transmucosal, epidural, intrathecal, and buccal administration.

The present invention contemplates a method of treating pain in a patient in need thereof, the method comprising administering an analgesic effective amount of a composition comprising a compound with the structure of formula (I) or a salt or derivative thereof to the patient, wherein the pain is moderate or severe.

DETAILED DESCRIPTION OF THE INVENTION

The present invention relates to a compound that has selectivity for $\mu$ opioid receptors as compared to $\delta$, $\kappa$, and ORL-1 receptors; compositions and unit dosage forms of the compound; and methods of using such compound, compositions, and unit dosage forms. The compound, N-but-3-enyl-norbuprenorphine, has the structure:

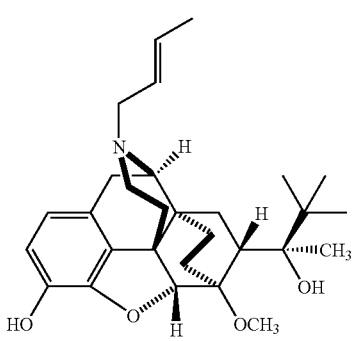
(I)

Without wishing to be bound by any particular theory, N-But-3-enyl-norbuprenorphine (I) has been found to be a partial agonist of the μ, δ, κ, and ORL-1 opioid receptors. A partial agonist is an agent that binds to, but does not fully stimulate, the receptor. In addition, the agent prevents the binding of a full agonist, thereby blocking the total pharmacologic activity possible from the receptor.

Certain preferred embodiments of the present invention are described below. In so far as the description refers to certain components of the invention with approximations, e.g., the terms "about" or "approximately", these terms shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Salts and Derivatives

Various pharmaceutically acceptable salts, ether derivatives, ester derivatives, acid derivatives, and aqueous solubility altering derivatives of the compound also are encompassed by the present invention. The present invention further includes all individual enantiomers, diastereomers, racemates, and other isomer ratios of the compound. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein. In so far as the application contemplates ether derivatives of formula (I), such derivatives may include C1–C6 lower alkyl or alkenyl, branched or unbranched ethers, optimally substituted by one or more heteroatoms, such as N, O, S, Si, or halogen-substituted lower (C1–C6) alkyl groups. With respect to ester derivatives of formula (I), such derivatives may include C1–C6 lower alkyl, branched or unbranched esters.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

The present invention includes prodrugs of the compound of the present invention. Prodrugs include, but are not limited to, functional derivatives of the compounds of the present invention which are readily convertible in vivo into the compound of the present invention, such as axetil and pivoxetil. Conventional procedures for the selection and preparation of suitable prodrug derivatives are described, for example, in "Design of Prodrugs", ed. H. Bundgaard, Elsevier, 1985.

In the context of this application, when reference is made to the compound of the invention, such a reference shall also include salts or derivatives of the compound of the invention.

Synthesis

The compound of the present invention may be prepared by any conventional methods known in the art. In one example, α-(1,1-dimethylethyl)-4,5-epoxy-18,19-dihydro-3-hydroxy-6-methoxy α-methyl, (αS,5α,7α)-6,14-ethenomorphinan-7-methanol (norbuprenorphine) (0.2 g, 0.47 mmole; available from Tasmanian Alkaloids (Tasmania), McFarlan Smith (U.K.); alternatively, norbuprenorphine can be prepared from buprenorphine using the scheme proposed by Duyang et al., *Trip Report: 222$^{nd}$ American Chemical Society National Meeting*, Chicago, Ill., Aug. 26–30 (2001), which can be found at http://www.albmolecular.com/features/tekreps/vol26/no58) may be reacted with a halo-alkene/alkane in the presence of a base and a solvent. The reaction can be conducted at a temperature of about 0° C. to about reflux temperatures for about 5 to about 48 hours. The ratio of norbuprenorphine to alkene/alkane may be from about 1:1 to about 1:10, with a ratio of 1:1 being preferred. In a preferred embodiment, the norbuprenorphine is reacted with 4bromo-1-butene in DMF and sodium bicarbonate. In a further embodiment, the reaction is conducted at 95° C. for 16 hours.

The reaction mixture is then cooled and concentrated to dryness under reduced pressure, and the residue is taken up in a non-polar solvent, and washed with water. An example of a non-polar solvent that may be used is, but is not limited to, methylene chloride. The resulting organic layer is dried (Na$_2$SO$_4$) and concentrated under reduced pressure. This material can be purified by any method known in the art. In a preferred embodiment, the product is purified by flash chromatography on silica gel (2% methanol in methylene chloride).

Pharmaceutical Compositions

The compound, salt, derivative and/or prodrug of the present invention may be formulated into a pharmaceutical composition. The pharmaceutical composition also may include additives, such as a pharmaceutically acceptable carrier, a flavorant, a sweetener, a preservative, a dye, a binder, a suspending agent, a dispersing agent, a colorant, a disintegrant, an excipient, a diluent, a lubricant, a plasticizer, an edible oil or any combination of any of the foregoing.

Suitable pharmaceutically acceptable carriers include, but are not limited to, ethanol, water, glycerol, aloe vera gel, allantoin, glycerin, vitamin A and E oils, mineral oil, PPG2 myristyl propionate, vegetable oils and solketal.

Suitable binders include, but are not limited to, starch, gelatin, natural sugars, such as glucose, sucrose and lactose, corn sweeteners, natural and synthetic gums, such as acacia, tragacanth, vegetable gum, and sodium alginate, carboxymethylcellulose, polyethylene glycol, waxes, and the like.

Suitable disintegrants include, but are not limited to, starch, such as corn starch, or methyl cellulose, agar, bentonite, xanthan gum and the like.

Suitable lubricants include, but are not limited to, sodium oleate, sodium stearate, magnesium stearate, sodium acetate, and the like.

The composition may also include suitable preservatives, e.g., sodium benzoate, and other additives the may render the composition more suitable for ingestion and or injection, e.g., sodium chloride, which affects the osmolarity of the preparation.

A suitable suspending agent is, but is not limited to, bentoite.

Suitable dispersing and suspending agents include, but are not limited to, synthetic and natural gums, such as vegetable gum, tragacanth, acacia, alginate, dextran, sodium carboxymethylcellulose, methylcellulose, polyvinyl-pyrrolidone and gelatin.

Suitable edible oils include, but are not limited to, cottonseed oil, corn oil, palm oil, sesame oil, coconut oil and peanut oil.

A suitable pharmaceutical diluent is, but is not limited to, water, saline, or lactated Ringer's solution.

Examples of additional additives include, but are not limited to, sorbitol, talc, stearic acid, and dicalcium phosphate.

Unit Dosage Fonts

The pharmaceutical compositions may be formulated as unit dosage forms, such as tablets, pills, capsules, boluses, powders, granules, sterile parenteral solutions, sterile parenteral suspensions, sterile parenteral emulsions, elixirs, tinctures, metered aerosol or liquid sprays, drops, ampoules, autoinjector devices or suppositories. Unit dosage forms may be used for oral, parenteral, intranasal, sublingual or rectal administration, or for administration by inhalation or insufflation, transdermal patches, and a lyophilized composition.

Solid unit dosage forms may be prepared by mixing the compound, salt or derivative of the present invention with a pharmaceutically acceptable carrier and any other desired additives as described above. The mixture is typically mixed until a homogeneous mixture of the compound of the present invention and the carrier and any other desired additives are formed, ie., until the compound is dispersed evenly throughout the composition.

Tablets or pills can be coated or otherwise compounded to form a unit dosage form which has delayed and/or prolonged action, such as time release and sustained release unit dosage forms. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release.

Biodegradable polymers for controlling the release of the compound, include, but are not limited to, polylactic acid, polyepsilon caprolactone, polyhydroxy butyric acid, polyorthoesters, polyacetals, polydihydro-pyrans, polyanhydrides, polycyanoacrylates, cross-linked or amphipathic block copolymers of hydrogels, cellulosic polymers, and polyacrylates.

Liquid unit dosage forms include, but are not limited to, aqueous solutions, suitably flavoured syrups, aqueous or oil suspensions, and flavored emulsions with edible oils, as well as elixirs and similar pharmaceutical vehicles. These dosage forms may be prepared by dissolving or suspending the compound of the present invention in the liquid carrier.

Topical preparations typically contain a suspending agent and optionally, an antifoaming agent. Such topical preparations may be liquid drenches, alcoholic solutions, topical cleansers, cleansing creams, skin gels, skin lotions, and shampoos in cream or gel formulations (including, but not limited to aqueous solutions and suspensions).

Administration

The pharmaceutical composition or unit dosage forms of the present invention may be administered by a variety of routes such as intraveneous, intratracheal, subcutaneous, oral, parenteral, buccal, sublingual, opthalmic, pulmonary, transmucosal, transdermal, and intramuscular. Unit dosage forms also can be administered in intranasal form via topical use of suitable intranasal vehicles, or via transdermal routes, using those forms of transdermal skin patches known to those of ordinary skill in the art.

Pharmaceutical compositions and unit dosage forms of the present invention for administration parenterally, and in particular by injection, typically include a pharmaceutically acceptable carrier, as described above. A preferred liquid carrier for depot forms is vegetable oil. Injection may be, for example, intravenous, epidural, intrathecal, intramuscular, intraruminal, intratracheal, or subcutaneous for purposes of depot delivery and sustained effect.

The compound, pharmaceutical compositions, or unit dosage forms of the present invention also can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compound of the present invention also may be delivered by the use of monoclonal antibodies as individual carriers to which the compound molecules are coupled.

The compound of the present invention may also be coupled with soluble polymers as targetable drug carriers.

Such polymers include, but are not limited to, polyvinylpyrrolidone, pyran copolymer, polyhydroxypropylmethacryl-amidephenol, polyhydroxyethylaspartamidephenol, and polyethyleneoxideopolylysine substituted with palmitoyl residues.

A transdermal dosage form also is contemplated by the present invention. Transdermal forms may be a diffusion-driven transdermal system (transdermal patch) using either a fluid reservoir or a drug-in-adhesive matrix system. Other transdermal dosage forms include, but are not limited to, topical gels, lotions, ointments, transmucosal systems and devices, and iontophoretic (electrical diffusion) delivery system. Transdermal dosage forms may be used for timed release and sustained release of the compound of the present invention.

The pharmaceutical compositions or unit dosage forms of the present invention may be administered to an animal, preferably a human being, in need thereof to agonize and/or antagonize activity of the μ receptors. The pharmaceutical composition may be used to treat various conditions, such as pain, cough, opiate withdrawal (abstinence syndrome) and/or drug addiction. The compound, pharmaceutical composition, or unit dosage form of the present invention may be administered alone at appropriate dosages defined by routine testing in order to obtain optimal interaction with the μ receptor or its activity while minimizing any potential toxicity.

The daily dosage of the compound of the present invention may vary according to a variety of factors such as underlying disease states, the individual's condition, weight, sex and age and the mode of administration. For oral administration, the pharmaceutical compositions can be provided in the form of scored or unscored solid unit dosage forms containing 0.01, 0.05, 0.1, 0.5, 1.0, 2.5, 5.0, 10.0, 15.0, 25.0, or 50.0 milligrams of the compound, salt or derivative of the present invention for the symptomatic adjustment of the dosage to the patient to be treated. An effective amount of the compound, salt or derivative may be supplied at a dosage level of from about 0.01 mg/kg to about 100 mg/kg of body weight per day. In a preferred embodiment, the effective amount of the compound, salt or derivative of the invention is administered by any appropriate method to achieve a blood concentration of from 20 pg/ml to 10 ng/ml.

In a preferred embodiment, an "analgesic effective amount" of the compound, salt or derivative of the invention is administered to the patient in need of analgesic treatment. An "analgesic effective amount" is that amount of the compound that reduces or alleviates pain in the patient, as determined by the degree of pain suffered by the patient, together with such factors as the height, weight, age, and condition of the patient, as well as the route of administration of the compound.

Alternatively, a "receptor agonizing effective amount" of the compound is administered to the patient in need thereof. Such an amount is that amount of the compound which binds to and stimulates receptor function.

The present invention also provides methods employing a "sedating effective amount" of the compound, salt or derivative of the invention. Such an amount is that amount that exerts a soothing or tranquilizing effect on the patient. A sedative may be general, local, nervous or vascular.

The compound, salt or derivative of the invention may be administered in an "antitussive effective amount," which is that amount of the compound, salt or derivative that reduces or relieves coughing in a patient, as determined by the height, weight, age, and condition of the patient, as well as the route of administration of the compound.

Finally, the compound, salt or derivative of the invention may also be administered in an "addiction-relieving effective amount" which is that amount of the compound, salt or derivative that reduces the desire of the patient for opiates.

Alternatively, the compound, salt or derivative of the invention may be administered in an "opioid withdrawal-relieving effective amount" which is that amount of the compound, salt or derivative that reduces the symptoms of abstinence syndrome in the patient.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the absorption, distribution, metabolism, and excretion of a drug.

The pharmaceutical composition or unit dosage form may be administered in a single daily dose, or the total daily dosage may be administered in divided doses of two, three or four times daily. In addition, co-administration or sequential administration of other active agents may be desirable. For combination treatment with more than one active agent, where the active agents are in separate dosage formulations, the active agents can be administered concurrently, or they each can be administered at separately staggered times. The dosage amount may be adjusted when combined with other active agents as described above to achieve desired effects. On the other hand, unit dosage forms of these various active agents may be independently optimized and combined to achieve a synergistic result wherein the pathology is reduced more than it would be if either active agent were used alone.

Generally, topical preparations contain from about 0.01% to about 100% by weight of the compound, salt or derivative, based upon 100% total weight of the topical preparation. In a preferred embodiment, topical preparations contain from about 0.1% to about 50% by weight of the compound, salt or derivative, and more preferably from about 1.0% to about 25% by weight of the compound, salt or derivative.

Generally, the pharmaceutical composition for parenteral administration contains from about 0.01% to about 90% by weight of the compound, salt or derivative of the present invention, based upon 100% weight of total pharmaceutical composition. In a preferred embodiment, preparations for parenteral administration contain from about 0.1% to about 50% by weight of the compound, salt or derivative, and more preferably from about 1.0% to about 25% by weight of the compound, salt or derivative.

Generally, transdermal dosage forms contain from about 0.01% to about 100% by weight of the compound, salt or derivative, based upon 100% total weight of the dosage. In a preferred embodiment, transdermal preparations contain from about 0.1% to about 50% by weight of the compound, salt or derivative, and more preferably from about 1.0% to about 25% by weight of the compound, salt or derivative.

Finally, the preparations or compositions of the present invention may contain the compound, salt or derivative as about 50% or more by weight of the active ingredient, preferably, about 75% or more, more preferably, 90% or more, 95% or more, 99% or more, 99.5% or more, or most preferably 99.9% or more by weight of active ingredient.

The present invention also contemplates kits comprising a compound or composition of the invention. In a preferred embodiment, such a kit contains a suitable container for the components of the kit, which may include, without limitation, an effective amount of the compound, salt or derivative or composition of the invention, tailored according to its intended use, as described above, as well as a label for the kit, and printed instructions for use of the compound or composition of the invention which are once again, tailored according to the intended use of the kit, such as, e.g., to treat or prevent pain, to induce sedation, to treat opiate addiction or withdrawal, and/or to treat cough.

EXAMPLES

Example 1

Synthesis of N-But-3-Enyl, Norbuprenorphine

To a suspension of α-(1,1-dimethylethyl)-4,5-epoxy-18,19-dihydro-3-hydroxy-6methoxy-α-methyl, (αS,5α, 7α)-6,14-ethenomorphinan-7-methanol (norbuprenorphine) (0.2 g, 0.47 mmole; available from Tasmanian Alkaloids (Tasmania)) in 2 mL of DMF was added sodium bicarbonate (0.146 g, 1.74 mmole) and 4-bromo-1-butene (0.064 g, 0.47 mmole). The reaction mixture was stirred at 95° C. for 16 hours. The cooled reaction mixture was concentrated to dryness under reduced pressure, and the residue was taken up in 10 ml methylene chloride and washed 3×10 mL with water. The resulting organic layer was dried (Na$_2$SO4) and concentrated under reduced pressure to yields a pale brown oil, which crystallized upon standing. This material was purified by flash chromatography on silica gel (2% methanol in methylene chloride) to yield 0.1 gram of the desired product as an off-white crystalline solid. FAB High Resolution Mass Spectrum m/z 468.3091 [M+1]$^+$, calculated 468.3114.

Example 2

Receptor Binding Studies

Delta$_2$ Binding Assay: The receptor source was a human recombinant cell line. The radioligand used in the studies was [$^3$H]-naltrindole. Binding reactions were conducted in 50 mM Tris-HCl (pH=7.4) containing 5 mM MgCl$_2$ at 25° C. for 60 minutes. The binding reactions were terminated by rapid vacuum filtration onto glass fiber filters. Radioactivity trapped onto the filters was determined and compared to control values.

Kappa Binding Assay: The receptor source was a human recombinant cell line. The radioligand used in the studies was [$^3$H]-diprenorphine. Binding reactions were conducted in 50 mM Tris-HCl (pH=7.4) containing 10 mM MgCl$_2$ and 1 mM EDTA at 25° C. for 60 minutes. The binding reactions were terminated by rapid vacuum filtration onto glass fiber filters. Radioactivity trapped onto the filters was determined and compared to control values.

Mu Binding Assay: The receptor source was a human recombinant cell line. The radioligand used in the studies was [$^3$H]-diprenorphine. Binding reactions were conducted in 50 mM Tris-HCl (pH=7.4) containing 10 mM MgCl$_2$ at 25° C. for 60 minutes. The binding reactions were terminated by rapid vacuum filtration onto glass fiber filters. Radioactivity trapped onto the filters was determined and compared to control values.

ORI-1 Binding Assay: The receptor source was a human recombinant cell line. The radioligand used in the studies was [$^3$H]-nociceptin. Binding reactions were conducted in 25 mM HEPES buffer (pH=7.4) containing 10 mM MgCl2 and 1 mM EDTA at 25° C. for 60 minutes. The binding reactions were terminated by rapid vacuum filtration onto glass fiber filters. Radioactivity trapped onto the filters was determined and compared to control values.

Ki values were determined using the Cheng-Pruss of equation. Results of the binding studies with various ligands are shown in Table 1.

TABLE 1

| | Ki values (nM) | | | |
|---|---|---|---|---|
| Compound | Delta | Kappa | Mu | ORL-1 |
| Buprenorophine | 1.9 | 0.157 | 1.33 | 218 |
| Norbuprenorphine | 856 | 31 | 1.36 | 1190 |
| Buprenorphine N-oxide | 16 | 14.8 | 3.11 | 31.3 |
| N-But-3-enylnorbuprenorphine | 113 | 15.4 | 0.224 | 2800 |

The binding data for N-but-3-enylnorbuprenorphine indicate highest affinity for mu, relatively high affinity for kappa, modest affinity for delta and low affinity for orphanin. Noteworthy is the activity for this compound at the mu receptor—it is six times more active than buprenorphine. Its activities at delta, kappa and orphanin receptors are less than buprenorphine by 60-fold, 100-fold and 20-fold, respectively.

Example 3

Opioid Receptor Binding and Functional Profile for
N-(3'-Butenyl)-Norbupren Rphine; Activity at the
Mu, Kappa, Delta and ORE-1 Receptors This in-vitro pharmacological study was initiated to assess the binding and functional properties of buprenorphine and its analog, N-(3'-Butenyl)-norbuprenorphine. The butenyl buprenorphine derivative, compared to buprenorphine, has an equally high affinity for the mu receptor and decreased affinity at the kappa, delta and ORL-1 receptors. Functional profiling of the N-(3-Butenyl)-norbuprenorphine compound has resulted in a rank order potency of mu >kappa≡delta>ORL-1. This compound is a partial agonist at all four opioid receptors, with the highest efficacy at the delta receptor.

A. Mu Opioid Receptor Binding

Radioligand dose-displacement assays used 0.2 nM [$^3$H]-diprenorphine (Perkin Elmer, Boston, Mass.; 50.0 Ci/mmole) with 20 μg membrane protein (recombinant mu opioid receptor expressed in CHO-K1 cells; Perkin Elmer) in a final volume of 500 μl binding buffer (10 mM MgCl$_2$, 1 mM EDTA, 5% DMSO, 50 mM Trizma base, pH 7.4). Unlabeled naloxone (Sigma) served as the assay positive control (concentration range 3×10$^{-7}$ to 1×10$^{-13}$ M). All reactions were performed in 96-deep well polypropylene plates for 2 h at room temperature. Binding reactions were terminated by rapid filtration onto 96-well Unifilter GF/C filter plates (Packard, Meriden, Conn.) presoaked in 0.5% polyethylenimine (Sigma). Harvesting was performed using a 96-well tissue harvester (Brandel) followed by three filtration washes with 500 μl ice-cold binding buffer. Filter plates were subsequently dried at 50° C. for 2–3 hours. Fifty μl/well scintillation cocktail (BetaScint; Perkin Elmer) was added and plates were counted in a Packard Top-Count for 1 min/well.

B. Kappa Opioid Receptor Binding

Radioligand dose-displacement assays used 0.40 nM [$^3$H]-U69,593 (Perkin Elmer; 41.4 Ci/mmole) with 20 µg membrane protein (recombinant kappa opioid receptor expressed in HEK 293 cells; Perkin Elmer) in a final volume of 500 µl binding buffer (5% DMSO, 50 mM Trizma base, pH 7.4). Unlabeled naloxone (Sigma) served as the assay positive control (concentration range $3\times10^{-6}$ to $3\times10^{-13}$ M). All reactions were performed in 96-well polypropylene plates for 1 h at room temperature. Binding reactions were terminated by rapid filtration onto 96-well Unifilter GF/C filter plates (Packard) presoaked in 0.5% polyethylenimine (Sigma). Harvesting was performed using a 96-well tissue harvester (Brandel) followed by five filtration washes with 500 µl ice-cold binding buffer. Filter plates were subsequently dried at 50° C. for 2–3 hours. Fifty µl/well scintillation cocktail (BetaScint; Perkin Elmer) was added and plates were counted in a Packard Top-Count for 1 min/well.

C. Delta Opioid Receptor Binding

Radioligand dose-displacement assays used 0.2 nM [$^3$H]-Naltrindole (Perkin Elmer; 33.0 Ci/mmole) with 12.5 µg membrane protein (recombinant delta opioid receptor expressed in CHO-K1 cells; Perkin Elmer) in a final volume of 200 µl binding buffer (5 mM $MgCl_2$, 5% DMSO, 50 mM Trizma base, pH 7.4). Unlabeled naloxone (Sigma) served as the assay positive control (concentration range $1\times10^{-5}$ to $1\times10^{-12}$ M). All reactions were performed in 96-well polypropylene plates for 1 h at room temperature. Binding reactions were terminated by rapid filtration onto 96-well Unifilter GF/C filter plates (Packard) presoaked in 0.5% polyethylenimine (Sigma). Harvesting was performed using a 96-well tissue harvester (Brandel) followed by five filtration washes with 200 µl ice-cold binding buffer. Filter plates were subsequently dried at 50° C. for 2–3 hours. Fifty µl/well scintillation cocktail (BetaScint; Perkin Elmer) was added and plates were counted in a Packard Top-Count for 1 min/well.

D. ORL-1 Opioid Receptor Binding

Membranes were prepared from recombinant HEK-293 cells expressing the human opioid receptor-like receptor (ORL-1) (Perkin Elmer) were prepared by lysing cells in ice-cold hypotonic buffer (2.5 mM $MgCl_2$, 50 mM HEPES, pH 7.4) (10 ml/10 cm dish) followed by homogenization with a tissue grinder/teflon pestle. Membranes were collected by centrifugation at 30,000× g for 15 min at 4° C. and pellets resuspended in hypotonic buffer to a final concentration of 1–3 mg/ml. Protein concentrations were determined using the BioRad protein assay reagent with bovine serum albumen as standard. Aliquots of the ORL-1 receptor membranes were stored at –80° C.

Radioligand binding assays used 0.1 nM [3H]-nociceptin (Perkin Elmer; 87.7 Ci/mmole) with 20 µg membrane protein in a final volume of 500 µl binding buffer (10 mM MgC12, 1 mM EDTA, 5% DMSO, 50 mM HEPES, pH 7.4). Unlabeled nociceptin (Sigma) served as the assay positive control (concentration range 2×10-7 to 6×10-13 M). All reactions were performed in 96-deep well polypropylene plates for 2 h at room temperature. Binding reactions were terminated by rapid filtration onto 96-well Unifilter GF/C filter plates (Packard) presoaked in 0.5% polyethylenimine (Sigma). Harvesting was performed using a 96-well tissue harvester (Brandel) followed by three filtration washes with 500 µl ice-cold binding buffer. Filter plates were subsequently dried at 50° C. for 2–3 hours. Fifty µl/well scintillation cocktail (BetaScint; Wallac) was added and plates were counted in a Packard Top-Count for 1 min/well.

E. Opioid Receptor [$^{35}$S]GTPγS Binding Functional Assays

Functional [$^{35}$S]GTPγS binding assays were conducted by sequentially mixing the following reagents in the order shown to yield the indicated final concentrations; (0.066 µg/µl ORL-1, 0.026 µg/µl Mu, 0.020 µg/µl Kappa or 0.012 µg/µl Delta) membrane protein, 10 µg/ml saponin, 3 µM GDP and 0.20 nM [$^{35}$S]GTPγS to binding buffer (100 mM NaCl, 10 mM $MgCl_2$, 20 mM HEPES, pH 7.4) on ice. The prepared membrane solution (190 µl/well) was transferred to 96-shallow well polypropylene plates containing 10 µl of 20× concentrated stock solutions of compound or appropriate control prepared in DMSO. Unlabeled DAMGO, U-69, 593, Met-Enkephalin, and Nociceptin (all from Sigma) served as the assay positive controls for the mu, kappa, delta and ORL-1 functional assays respectively. Plates were incubated for 30 min at room temperature with shaking. Reactions were terminated by rapid filtration onto 96-well Unifilter GFAB filter plates (Packard) using a 96-well tissue harvester (Brandel) and followed by three filtration washes with 200 µl ice-cold binding buffer (10 mM $NaH_2PO_4$, 10 mM $Na_2HPO_4$, pH7.4). Filter plates were subsequently dried at 50° C. for 2–3 hours. Fifty µl/well scintillation cocktail (BetaScint; Wallac) was added and plates were counted in a Packard Top-Count for 1 min/well.

Data from both binding and functional assays were analyzed using the curve fitting functions in GraphPad PRISM™, v. 3.0. Data were expressed as mean ±S.E.M.

F. Opioid Receptor Binding Results (i) Mu Opioid Receptor Binding Results

Buprenorphine and its butenyl derivative were equipotent in this assay with $K_i$ values of 0.30 and 0.38 nM respectively. The mu opioid receptor binding summary is outlined in Table 2.

(ii) Kappa Opioid Receptor Binding Results

The naloxone assay control for this assay gave an expected average Ki value of 3.7 nM The Ki value for buprenorphine was 0.036 nM which is approximately 10 times more potent than the butenyl derivative which gave a Ki value of 0.34 nM. The kappa opioid receptor binding summary is outlined in Table 2.

(iii) Delta Opioid Receptor Binding Results

The naloxone control performed within the expected range. The binding affinities for buprenorphine and the butenyl buprenorphine were 6.5 and 365 nM respectively. The delta opioid receptor binding summary is outlined in Table 2.

(iv) ORL-1 Opioid Receptor Binding Results

The nociceptin assay control gave a typical Ki value of 0.30 nM. The binding affinities for buprenorphine and its derivative were 40 and 1025 nM respectively. The ORL-1 opioid receptor binding summary is outlined in Table 2.

TABLE 2

In-Vitro Binding Profile

| Compound | Binding $K_i$ Values (nM) | | | |
| --- | --- | --- | --- | --- |
| | Mu $K_i$ | Kappa $K_i$ | Delta $K_i$ | ORL-1 $K_i$ |
| Naloxone Control | 1.2 ± 0.2 | 3.7 ± 0.9 | 625 ± 168 | nd |
| Nociceptin Control | nd | nd | nd | 0.30 ± 0.01 |
| Buprenorphine | 0.30 ± 0.14 | 0.036 ± 0.006 | 6.6 ± 1.4 | 40 ± 8 |
| N-(3'-Butenyl)-norbuprenorphine | 0.38 ± 0.12 | 0.34 ± 0.05 | 365 ± 134 | 1025 ± 214 |

(v) Opioid Receptor [$^{35}$S]GTIγS Binding Functional Assay Results

The butenyl derivative did not display as high potency to the receptors in the functional assay as buprenorphine.

However, the butenyl derivative was slightly more efficacious at the mu, kappa and ORL-1 receptors. None of the efficacy values exceeded 50%. The mu, kappa, delta and ORL-1 opioid receptor functional summaries are outlined in Table 3.

is 6-, 31- and 11-fold more potent at the mu, kappa and delta receptors, respectively. The higher buprenorphine potency is not reflected in the efficacy rank order. The butenyl derivative is slightly more efficacious at the mu, kappa and delta receptors. It is the most efficacious at the delta receptor

TABLE 3

In-Vitro Functional Profile

Functional GTPgS Activity (nM)

| Compound | Mu | | Kappa | | Delta | | ORL-1 | |
|---|---|---|---|---|---|---|---|---|
| | $EC_{50}$ | Efficacy % DAMGO | $EC_{50}$ | Efficacy % U-69,593 | $EC_{50}$ | Efficacy % Met-Enk | $EC_{50}$ | Efficacy % Noci |
| DAMGO Control | 130 ± 11 | 100 ± 0% | nd | | nd | | nd | |
| Nociceptin Control | nd | | nd | | nd | | 0.60 ± 0.21 | 100 + 0% |
| U-69,593 Control | nd | | 37 ± 9 | 100 ± 0% | nd | | nd | |
| Met-Enkephalin Control | nd | | nd | | 9.3 ± 2.2 | 100 ± 0% | | |
| Buprenorphine | 0.45 ± 0.08 | 12 ± 1% | 0.56 ± 0.17 | 11 ± 0% | 3.3 ± 0.3 | 12 ± 1% | 325 ± 123 | 36 ± 3% |
| N-(3'-Butenyl)-norbuprenorphine | 3.0 ± 0.9 | 28 ± 4% | 19 ± 4 | 16 ± 1% | 32 ± 9 | 47 ± 0% | 448 ± 49 | 19 ± 2% |

TABLE 4

In-Vitro Pharmacological Profile

| Compound | Binding $K_1$ Values (nM) | | | | Functional GTPgS Activity (nM) Mu | | Functional GTPgS Activity (nM) Kappa | | Functional GTPgS Activity (nM) Delta | | Functional GTPgS Activity (nM) ORL-1 | |
|---|---|---|---|---|---|---|---|---|---|---|---|---|
| | Mu $K_1$ | Kappa $K_1$ | Delta $K_1$ | ORL-1 $K_1$ | $EC_{50}$ | Efficacy % DAMGO | $EC_{50}$ | Efficacy % U-69,593 | $EC_{50}$ | Efficacy % Met-Enk | $EC_{50}$ | Efficacy % Noci |
| Naloxone Control | 1.2 ± 0.2 | 3.7 ± 0.9 | 625 ± 168 | nd | nd | | nd | | nd | | nd | |
| DAMGO Control | nd | nd | nd | nd | 130 ± 11 | 100 ± 0% | nd | | nd | | nd | |
| Nociceptin Control | nd | nd | nd | 0.30 ± 0.01 | nd | | nd | | nd | | 0.60 ± 0.21 | 100 + 0% |
| U-69,593 Control | nd | nd | nd | nd | nd | | 37 ± 9 | 100 ± 0% | nd | | nd | |
| Met-Enkephalin Control | nd | nd | nd | nd | nd | | nd | | 9.3 ± 2.2 | 100 ± 0% | nd | |
| Buprenorphine | 0.30 ± 0.14 | 0.036 ± 0.006 | 6.6 ± 1.4 | 40 ± 8 | 0.45 ± 0.08 | 12 ± 1% | 0.56 ± 0.17 | 11 ± 0% | 3.3 ± 0.3 | 12 ± 1% | 325 ± 123 | 36 ± 3% |
| N-(3'-Butenyl)-norbuprenorphine | 0.38 ± 0.12 | 0.34 ± 0.05 | 365 ± 134 | 1025 ± 214 | 3.0 ± 0.9 | 28 ± 4% | 19 ± 4 | 16 ± 1% | 32 ± 9 | 47 ± 0% | 448 ± 49 | 19 ± 2% |

These experiments show that the N-(3'-Butenyl)-norbuprenorphine binds the same receptors as the buprenorphine control. This butenyl compound compared to buprenorphine has a lower binding affinity for all of the receptors except for mu where they are equipotent. Buprenorphine displays the highest affinity for the kappa receptor, followed by mu, delta and ORL-1, whereas, the butenyl derivative binds the mu and kappa receptor equipotently, followed by delta then ORL-1.

Functionally, buprenorphine and the butenyl compound have agonist effects at the receptors in the same rank order of potency (mu>kappa>delta>ORL-1). While the two compounds are equipotent at the ORL-1 receptor, buprenorphine (47%). Both compounds act as partial agonists with none of the efficacies exceeding 50% of control.

The present invention is not to be limited in scope by the specific embodiments described herein. Indeed, various modifications of the invention in addition to those described herein will become apparent to those skilled in the art from the foregoing description and any accompanying figures. Such modifications are intended to fall within the scope of the appended claims.

Patents, patent applications, publications, procedures, and the like are cited throughout this application, the disclosures of which are incorporated herein by reference in their entireties.

What is claimed is:

1. A compound having the structure:

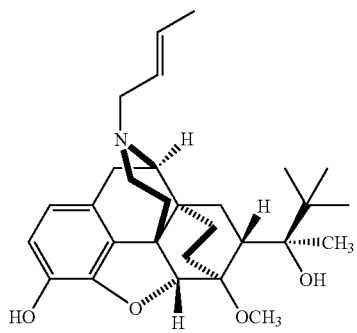

pharmaceutically acceptable salt, aqueous, enantiomer, diastereomer, racemate, polymorph, or solvate thereof.

2. A composition comprising a compound as defined in claim 1.

3. A composition as defined in claim 2, further comprising:
(a) an adjuvant; (b) an anti-oxidant; (c) a buffer; (d) a carrier; (e) a colorant; (f) a diluent; (g) a disintegrant; (h) an excipient; (i) a filler; (j) a flavorant; (k) a gelling agent; (l) a lubricant; (m) a neutralizing agent; (n) a preservative; or (o) any combination of any of the foregoing.

4. A composition as defined in claim 3, comprising an opiate receptor agonizing effective amount of said compound.

5. A composition as defined in claim 4, wherein said opiate receptor is a μ receptor.

6. A composition as defined in claim 3, comprising an analgesic effective amount of said compound.

7. A composition as defined in claim 3, comprising a sedative effective amount of said compound.

8. A composition as defined in claim 3, comprising an anti-tussive amount of said compound.

9. A composition as defined in claim 3, comprising an opioid withdrawal-relieving effective amount of said compound.

10. A composition as defined in claim 3, comprising an opioid addiction-relieving effective amount of said compound.

11. A composition as defined in claim 1, comprising 50% or more by weight of said compound.

12. A composition as defined in claim 1, comprising 90% or more by weight of said compound.

13. A composition as defined in claim 1, comprising 99.9% or more by weight of said compound.

14. A composition as defined in claim 3, comprising said compound in an amount sufficient to achieve a maximum blood concentration of from about 20 pg/ml to about 10 ng/ml of said compound.

15. A unit dosage form comprising a composition as defined in claim 2.

16. A unit dosage form as defined in claim 15, selected from the group consisting of tablets, pills, capsules, boluses, powders, granules, sterile parenteral solutions, sterile parenteral suspensions, elixirs, tinctures, metered aerosol, liquid sprays, drops, ampoules, autoinjector devices, suppositories, transdermal patches, and a lyophilized composition.

17. A unit dosage form as defined in claim 15, which is a sustained release unit dosage form.

18. A unit dosage form as defined in claim 15, comprising 50% or more by weight of said compound.

19. A unit dosage form as defined in claim 15, comprising 90% or more by weight of said compound.

20. A unit dosage form as defined in claim 15, comprising 99.9% or more by weight of said compound.

* * * * *

UNITED STATES PATENT AND TRADEMARK OFFICE
CERTIFICATE OF CORRECTION

| | | |
|---|---|---|
| PATENT NO. | : 7,125,884 B2 | Page 1 of 1 |
| APPLICATION NO. | : 10/469553 | |
| DATED | : October 24, 2006 | |
| INVENTOR(S) | : Bruce E. Reidenberg et al. | |

It is certified that error appears in the above-identified patent and that said Letters Patent is hereby corrected as shown below:

On Title Page item 86
In the Filing Date:

Please delete "Aug. 29, 2003" and substitute -- Oct. 29, 2003 --.

Signed and Sealed this

Ninth Day of January, 2007

JON W. DUDAS
*Director of the United States Patent and Trademark Office*